United States Patent
Salles

(10) Patent No.: US 6,656,497 B2
(45) Date of Patent: *Dec. 2, 2003

(54) LIPOSOMAL VECTOR FOR ACTIVE-PRINCIPLE

(75) Inventor: Jean-Pierre Salles, Eguilles (FR)

(73) Assignee: Lipogel, Allauch (FR)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/445,444
(22) PCT Filed: Jun. 11, 1998
(86) PCT No.: PCT/FR98/01204
§ 371 (c)(1),
(2), (4) Date: Feb. 17, 2000
(87) PCT Pub. No.: WO98/56352
PCT Pub. Date: Dec. 17, 1998

(65) Prior Publication Data

US 2002/0146447 A1 Oct. 10, 2002

(30) Foreign Application Priority Data

Jun. 11, 1997 (FR) .............................. 97 07255

(51) Int. Cl.[7] .................. A61K 9/127; A61K 9/133
(52) U.S. Cl. ................ 424/450; 424/489; 424/490; 424/499; 428/402.2; 264/4.1; 264/4.3; 514/2; 514/21; 514/45; 514/824
(58) Field of Search .................. 424/450, 1.21, 424/9.51, 417, 812, 489–502; 428/402.2; 264/4.1, 4.3

(56) References Cited

U.S. PATENT DOCUMENTS 5,626,870 A  *  5/1997  Monshipouri et al.
5,783,211 A  *  7/1998  Manzo et al.

FOREIGN PATENT DOCUMENTS

WO          87/01586   *  3/1987
WO     WO 87/01587 A      3/1987
WO     WO 95 27477 A     10/1995

OTHER PUBLICATIONS

J. Microencapsulation, 1995; vol. 12; No. 3; "Factors affecting microencapsulation of drugs in liposomes" S.B. Kulkarni, et al.; pp. 229–246.
BNA's Intellectual Property Library on CD– Full Text of Cases (USPQ First Series); In re Oda, Fujii, Moriga, and Higaki; pp. 1–11.

* cited by examiner

Primary Examiner—Gollamudi S. Kishore
(74) Attorney, Agent, or Firm—Oblon, Spivak, McClelland, Maier & Neustadt, P.C.

(57) ABSTRACT

The invention concerns liposome vectors, in powder form, of active principles, and more particularly active principles sensitive to digestive and/or plasmatic degradation, such as proteins, and their application as medicine. Said liposome vectors of active principles consist of a powder composition essentially constituted of unilamellar liposomes comprising an external lipid phase consisting of class 4 lipids (phospholipids), optionally associated with class 2 substances, class 3 substances and/or class 5 substances and an internal aqueous nucleus consisting of a mixture M of at least two different non-polymerisable gelling agents (G1 and G2) whereof the gel-sol phase transition is not less than 37° C., G1 being selected among gelatines and carrageenans and G2 being selected among carrageenans with properties different from the carrageenans selected for G1, and celluloses, which liposomes have a diameter ranging between 20 nm and 1 mm, preferably between 20 nm and 500 nm; said composition having the form of particulate units with an average particle diameter between 10 mm and 1000 mm, formed by one or several of said liposomes, enclosed in a sheath selected in the group consisting of a dehydrated thermoreversible aqueous gel identical to said internal nucleus aqueous gel, dextrins or a mixture thereof, such that they contain, on an average, 10 to 10 liposomes per gram of powder; and at least an active principle contained, as the case may be, either in the gelled internal nucleus or in the external lipid phase.

19 Claims, 5 Drawing Sheets

LIPOSOMAL VECTOR FOR ACTIVE-PRINCIPLE

This application is a 371 of Pct/Fr98/01204 filed on Jun. 11, 1998.

BACKGROUND OF THE INVENTION

1. Field of the Invention

The present invention relates to stable liposomal vectors, in pulverulent form, for active principles, and more particularly for active principles which are sensitive to digestive and/or plasmatic degradation, such as proteins, and to their use as medicinal products.

2. Description of the Background

Many vectors have been proposed to protect such fragile active principles; among these, mention should be made of liposomes, which have been considered as a vector of choice.

The first studies on the oral administration of liposomes were not conclusive (Deshmukh D. S. et al., Life Sciences, 1981, 28, 239–242). The results obtained showed that liposomes with the formulation: diether-phosphatidylcholine (indigestible PC analogues)/cholesterol-7:1 allowed gastrointestinal protection of the encapsulated peptide, but did not allow its passage across the intestinal barrier.

Several reasons may be put forward to explain this absence of passage: excessively large and non-calibrated size of the liposomes, low stability of the structure or leakage of the encapsulated compound into the extraliposomal medium.

Recently, the research team of Robert Greenwood (*Drug Dev. and Ind. Pharm.*, 1993, 19, 11, 1303–1315) at the Campbell University, U.S.A., has succeeded in showing that the duodenal intubation of liposomes vectorizing insulin brought about a higher hypoglycaemiant effect than that obtained after a duodenal intubation of a solution of free insulin.

Many tests have been carried out to obtain liposomes with good capacity to transport active principles, in particular as regards the action on the percentage of uptake of the active principle, the stability of the liposomes and the bioavailability of the active principle. Mention may be made, for example, as a guide, of:

S. B. Kulkarni et al. (*J. Microencapsulation*, 1995, 12, 3, 229–246) who point out the factors involved in the microencapsulation of medicinal products in liposomes: size of the liposome, type of liposome, surface charge of the liposome, rigidity of the bilayer, addition of encapsulation adjuvants. It emerges from this evaluation that MLVs (multilamellar vesicles) containing several bilayers and with a diameter of between 100 nm and 20 mm are desirable for the encapsulation of hydrophobic medicinal products interacting with the bilayers, whereas LUVs (large unilamellar vesicles) containing a single bilayer and with a size of between 100 and 1000 nm are considered as being the most suitable for the encapsulation of hydrophilic medicinal products.

I. De Miguel et al., (Biochimica et Biophysica Acta, 1995, 1237, 49–48 [sic]), who propose nanoparticles composed of an internal core formed from crosslinked polysaccharides grafted on their exterior with fatty acids and surrounded by a layer of phospholipids;

P. S. Uster et al., (*FEBS Letters*, 1996, 386, 243–246) who propose the insertion of phospholipids modified with a poly(ethylene glycol) in preformed liposomes to improve the bioavailability.

Series of experiments relating to the oral administration of peptides have been carried out and use either different liposomal methods of encapsulation, or modification of the lipidic active principle by grafting lipophilic functions. In all cases, the aim is to convert the lipidic active principle into a "prodrug"; this prodrug has the property of withstanding gastrointestinal transit, i.e. resistance to gastric pH, to physiological detergents (bile salts), to proteases (intestinal exopeptidases and endopeptidases) and to metabolization by the intestinal flora. For example, the bridging in position 2 of a 1,3-diglyceride onto a pentapeptide made it possible to impart these qualities to the drug thus modified.

However, these various liposomes of the prior art do not make it possible to obtain both good stability, an acceptable active-principle encapsulation yield and a significantly improved oral bioavailability of the said active principle, without modifying the active principle, which thus conserves all of its functions and properties. The term "bioavailability" means the fraction of the dose which reaches the systemic circulation in pharmacologically active form and the rate at which it does so.

J. C. Hauton has described liposomes with a gelatinized internal core (lipogelosomes®) which are in suspension in aqueous medium containing gelatinizing substances. He has, in particular, developed a process for manufacturing such liposomes (European patent 0 393 049), which differ from conventional liposomes in that the encapsulated aqueous phase is in semi-solid gel form rather than in liquid form, and this prevents the liposomes from fusing during collisions. Such lipogelosomes® are produced entirely from natural substances, thereby minimizing the risk of intolerance. In particular, in European patent 0 393 049, these lipogelosomes® consist of one bilayer interfacial phase, in the case of the unilamellar lipogelosomes, or of a plurality of bilayer interfacial phases, which are superimposed concentrically, in the case of the multilamellar lipogelosomes®, and of a gelatinized encapsulated internal aqueous polar phase in which the gelatinized substance, which may or may not be polymerizable, is selected from polysaccharides, polypeptides or polyacrylamides; for example, the non-polymerizable gelatinizable substance is selected from gelatin, agarose or carrageenans, and the polymerizable gelatinizable substance is selected from polyacrylamide gels. These lipogelosomes® possess a stability which is significantly increased as compared with the liposomes of the prior art, particularly because of the absence of interparticulate fusion during collisions.

However, they suffer from the drawback of being in the form of a dispersion of liposomes in liquid phase, which is not suitable for preparing solid formulations which are easy to store and to administer.

SUMMARY OF THE INVENTION

Consequently, the Applicant set itself the objective of providing a novel vector which effectively makes it possible to obtain both a sufficient encapsulation yield and significantly improved oral bioavailability of the said active principle, compared with the liposomes of the prior art, while at the same time displaying great stability both on storage and in vivo. Said vectors are suited to oral administration; the aqueous solution is also suitable for other routes of administration: transdermal, pulmonary, nasal, genital, intravenous, subcutaneous or ocular, for example, depending on the excipient selected.

The said vectors are characterized in that they consist of:
a pulverulent composition which consists essentially of unilamellar liposomes comprising an external lipid phase which consists of class 4 lipids (phospholipids), optionally combined with class 2 substances (long-chain triglycerides, cholesterol esters), class 3 substances (cholesterol, nonionized long-chain fatty acids) and/or class 5 substances (bile salts, fusidic acid derivatives) and an internal aqueous core forming a temperature-reversible aqueous gel which radiates out up to the external lipid phase, which internal aqueous core essentially consists of a mixture M of at least two different non-polymerizable gelatinizing agents G1 and G2 whose gel-sol phase transition point is higher than or equal to 37° C., with G1 being a gelatinizing agent which is selected from gelatins and carrageenans, such as kappa-carrageenans, and G2 being selected from carrageenans whose properties are different from the carrageenans selected for G1, such as iota-carrageenans, and celluloses, such as hydroxypropylmethylcellulose, which liposomes have a diameter of between 20 nm and 1 mm, preferably of between 20 nm and 500 nm and being in the form of particulate units with an average diameter of between 10 mm and 1000 mm, formed from one or more of the said liposomes, surrounded by a matrix selected from the group consisting of a dehydrated temperature-reversible aqueous gel which is identical to the aqueous gel of the said internal core, dextrins or a mixture thereof, such that it comprises, on average, $10^{16}$ to $10^{18}$ liposomes/g of powder, and at least one active principle included, depending on the case, either in the gelatinized internal core or in the external lipid phase of the said composition.

DETAILED DESCRIPTION OF THE PREFERRED EMBODIMENTS

Surprisingly, such vectors make it possible to overcome the drawbacks associated with conventional liposomes. Specifically, they make it possible:

to increase the stability of the liposomes, on account of the absence of interparticulate fusion during collisions;

to increase the bioavailability of the active principle (protection in the gastrointestinal tract and passage across the intestinal barrier); in particular, in rats, the passage time of the vectors according to the invention (LGS) across the intestinal barrier from the moment of their oral administration can be between 2 and 4 hours: i.e. 1 hour of gastric emptying and 1 to 3 hours of passage from the intestinal lumen into the systemic circulation; thus, an active principle whose cellular internalization capacity is low or non-existent can be incorporated effectively into a differentiated intestinal epithelial cell, when it is encapsulated in a vector (LGS) according to the invention, without modifying the activity or composition of the active principle;

to reduce the toxicity of the the encapsulated active principles; and to result in fewer leakages of the encapsulated products, on account of the lower molecular mobility in the gelatinized encapsulated aqueous phase.

Unexpectedly, by selecting the gelatinizing agents, it is possible to obtain liposomes (SUVs or small unilamellar vesicles), which are suitable for use in a dry form (powder) and which have particularly advantageous properties as vectors for active principles; in specific terms, surprisingly, the oral bioavailability of the said active principles—preferably of active principles which are sensitive to digestive degradation, poorly absorbed or highly toxic—is significantly increased when they are encapsulated or combined with the vector according to the present invention.

In addition, such vectors in pulverulent form conserve all the integrity of the liposomes they contain, which remain stable over time, both in pulverulent form and when they are suspended, on account of the maintenance of the integrity of the constituent lipids (no degradation product) and the maintenance of the integrity of the characteristics of the gelatinizing agents, in particular of the mixture G1 and G2 (viscosity, gel strength and breaking force, molecular masses).

The advantage of using lipogelosomes® (LGS) in this context is that of benefiting from a stabilized liposomal form (J C Hauton et al., *Eur. J. Surg.*, 1994, suppl. 574, 117–119) for the purpose of the oral administration of active principles. The method for manufacturing LGSs makes it possible to obtain, on average, degrees of encapsulation of the gelatinized hydrophilic phases of close to 10%. This percentage varies, in particular as a function of the molecular weight of the active principle, and is calculated according to the ratio: amount of active principle encapsulated/amount of active principle used. For example, at least 5% encapsulation is observed for a 500 Da molecule and at least 50% encapsulation is observed for a molecule of at least 20 kDa. As regards peptides, for example, 10 to 50% encapsulation is observed, whereas, in general, for active principles as a whole, the percentage of encapsulation ranges from 5 to 80%, depending on the case.

The gelatinizing agents G1 and G2 differ in particular as regards the viscosity, molecular mass and gel-sol transition point (i.e. the melting point). For the gelatinizing agents C1, this temperature is less than or equal to 45° C., whereas it is greater than or equal to 45° C. for the gelatinizing agents G2.

The mixture M of at least two gelatinizing agents G1 and G2 as defined above has texturometric characteristics (gel strength and breaking force) which are particularly advantageous from the point of view of the stability of the liposomes obtained and the bio-availability of the encapsulated active principle. Thus, the mixture M of at least two gelatinizing agents G1 and G2 preferably has, at 5° C., relaxation characteristics of between 70 and 100%, preferably 81–89% and a breaking force of between 1000 and 1600 g, preferably 1109–1503 g.

According to another advantageous embodiment of the said composition, the said internal aqueous core of the liposomes also comprises at least one stabilizer of glycosidic nature, and/or at least one agent for regulating the osmolarity of the medium and/or at least one surfactant, such as a bile salt and/or a nonionic surfactant.

Advantageously, the said vectors comprise, as % (m/m): 25 to 75% of class 4 lipids, 5 to 45% of gelatinizing agents, 0 to 70% of stabilizer of glycosidic nature, 0 to 15% of agent for regulating the osmolarity of the medium, 0 to 20% of surfactants and 0 to 15% of dextrins, preferably 8 to 12%; this formulation does not include the active principles.

According to another advantageous embodiment of the said pulverulent composition according to the invention, the said aqueous internal core comprises 70 to 95% of gelatinizing agent G1 and 5 to 30% of gelatinizing agent G2.

According to another advantageous embodiment of the said pulverulent composition according to the invention, the stabilizer of glycosidic nature is sucrose, trehalose or any other protective agent.

The subject of the present invention is also a process for preparing the pulverulent vectors according to the invention, in which the external matrix of the particulate units comprises a fraction of temperature-reversible aqueous gel, characterized in that it comprises the following steps:

(1) preparation of a dispersion of liposomes with a gelatinized internal core (lipogelosomes®) in aqueous phase by (a) preparing a solution of at least one suitable gelatinizing agent, in particular a mixture M of gelatinizing agents G1 and G2, by dissolving the said gelatinizing agents, with slow stirring, at a temperature above the gel-sol phase transition temperature of the said gelatinizing agents, in an aqueous solution whose pH is compatible with the active principle to be encapsulated, (b) incorporating the active principle into the solution obtained in (a), (c) incorporating the lipids into the solution obtained in (b), with slow stirring of the mixture, for a period of less than 5 hours, preferably under vacuum, and formation of an emulsion, and (d) obtaining the said dispersion of liposomes with a gelatinized internal core (lipogelosomes®) in an aqueous phase containing the said gelatinizing agents, by rapid stirring of the emulsion obtained in (c), preferably under vacuum, and (2) production of the pulverulent product by suitable drying of the dispersion obtained.

According to one advantageous embodiment of the said process, the drying is carried out by atomization, coacervation, thin layer or granulation.

Another subject of the present invention is a process for preparing the pulverulent vectors according to the invention, in which the external matrix of the particulate units comprises a fraction of temperature-reversible aqueous gel and/or a dextrin, characterized in that it comprises the following steps:

(1) preparation of a dispersion of liposomes with a gelatinized internal core (lipogelosomes®) in aqueous phase by (a) preparing a solution of at least one suitable gelatinizing agent, in particular a mixture M of gelatinizing agents G1 and G2, by dissolving the said gelatinizing agents, with gentle stirring, at a temperature above the gel-sol phase transition temperature of the said gelatinizing agents, in an aqueous solution whose pH is compatible with the active principle to be encapsulated, (b) incorporating the active principle into the solution obtained in (a), (c) incorporating the lipids into the solution obtained in (b), with slow stirring of the mixture, for a period of less than 5 hours, preferably under vacuum, and formation of an emulsion, and (d) obtaining the said dispersion of liposomes with a gelatinized internal core (lipogelosomes®) in an aqueous external phase containing the said gelatinizing agents, by rapid stirring of the emulsion obtained in (c), preferably under vacuum, and (2) at least partial removal of the aqueous liquid phase containing the said gelatinizing agents, in which the liposomes are dispersed, (3) addition of at least one suitable dextrin, and (4) production of the pulverulent product by drying by atomization of the product obtained in (3).

According to one advantageous embodiment of the said process, step (2) of at least partially removing the aqueous liquid phase containing the said gelatinizing agents is carried out by dilution and/or filtration.

In accordance with the preparation processes according to the invention, the aqueous solution in step (a) also comprises an agent for regulating the osmolarity of the medium (for example 0.9% NaCl) and/or a stabilizer of glycosidic nature and/or a surfactant, preferably class 5 substances (bile salts).

As a variant, the active principle is added to the external lipid phase before it is incorporated into the mixture obtained in (a).

For example, calcitonin is incorporated at pH 5, AZT is incorporated at pH 7.5 and doxorubicin is incorporated at pH 3.

Surprisingly, such processes make it possible to obtain a vector in pulverulent form based on stable liposomes with a gelatinized internal core (lipogelosomes®) in the course of a single step comprising a phase of maturation (in the sense of ripening) of the constituents in aqueous phase, at slow speed, followed by a phase of dispersion (formation of the lipogelosomes®) at high speed, comprise a step during which a stable dispersion of lipogelosomes® in liquid phase, of homogeneous morphology, is obtained, which can be subjected to the drying step; such a dispersion of liposomes with a gelatinized internal core effectively has the following morphology:

vesicular structure with a diameter of between 20 nm and 500 nm, preferably between 20 and 80 nm, negative staining microscopic observations, cryofracture, cryotransmission and atomic force: vesicles or assemblies of vesicles with the characteristic appearance of phospholipid bilayers; negative staining makes it possible to observe the more or less pronounced presence of a mixture M of gelatinizing agents enveloping the external phospholipid layer, and polydispersity of the liposomes with a gelatinized internal phase of between 10 and 55%, preferably between 10 and 30%.

Such a process has the advantage of being reproducible and fully adaptable to the industrial scale.

It also has the advantage of being less cumbersome to implement than the processes of the prior art in which a step of sonication, extrusion or removal of detergents is necessary, as described in patent 0 393 049.

According to one advantageous embodiment of the said processes, the step (c) is preferably carried out at a shear rate of less than 200 $s^{-1}$; in general, the shear rate is given by the following ratio: speed of the stirring unit/space between the internal wall of the reactor and the distal end of the stirring blade (also known as the "air gap").

Another subject of the present invention is a pharmaceutical composition, characterized in that it comprises a pulverulent liposomal active-principle vector as defined above and at least one pharmaceutically acceptable vehicle.

According to one advantageous embodiment of the said composition, it is in solid form (gel capsule, tablet or powder to be dissolved in water).

According to another embodiment of the said composition, it also comprises a cAMP activator.

BRIEF DESCRIPTION OF THE DRAWINGS

Besides the preceding arrangements, the invention also comprises other arrangements, which will become apparent from the description which follows, with reference to the examples of implementation of the process which is the subject of the present invention, as well as to the attached drawings, in which:

FIG. 1 represents the variations in calcaemia as a function of time (-D-=free calcitonin; -■-=LGS-calcitonin vector according to the invention);

FIG. 2 represents the difference in AUC between the calcaemia obtained with free calcitonin and that obtained after oral administration of the LGS-calcitonin vectors according to the invention;

Figure 6:
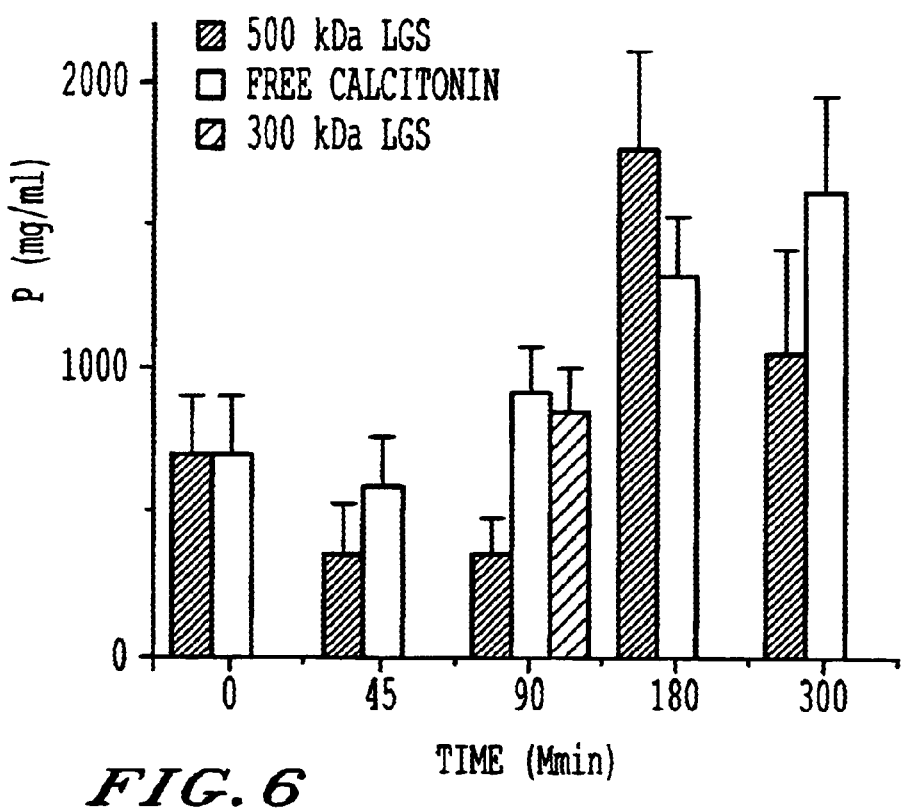
Figure 7:
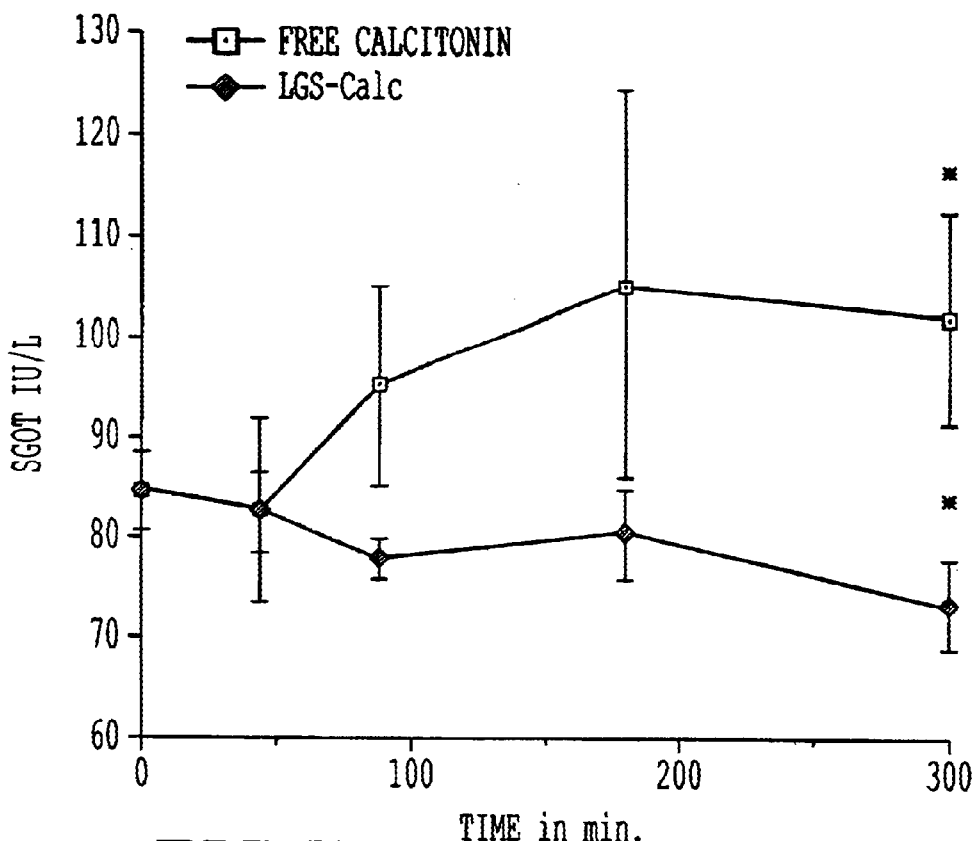
Figure 8:
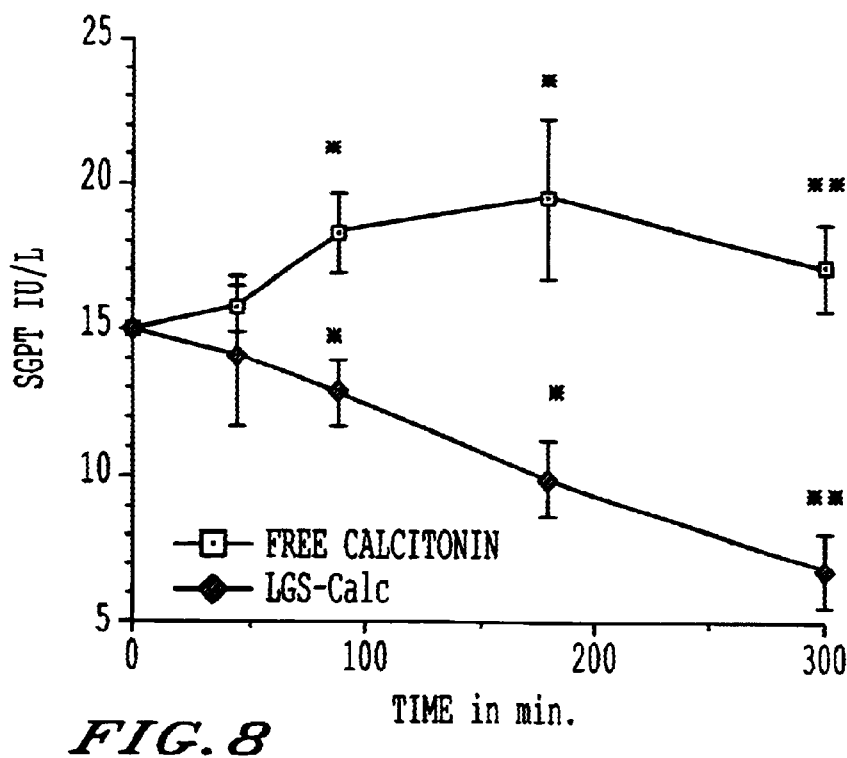
Figure 9:
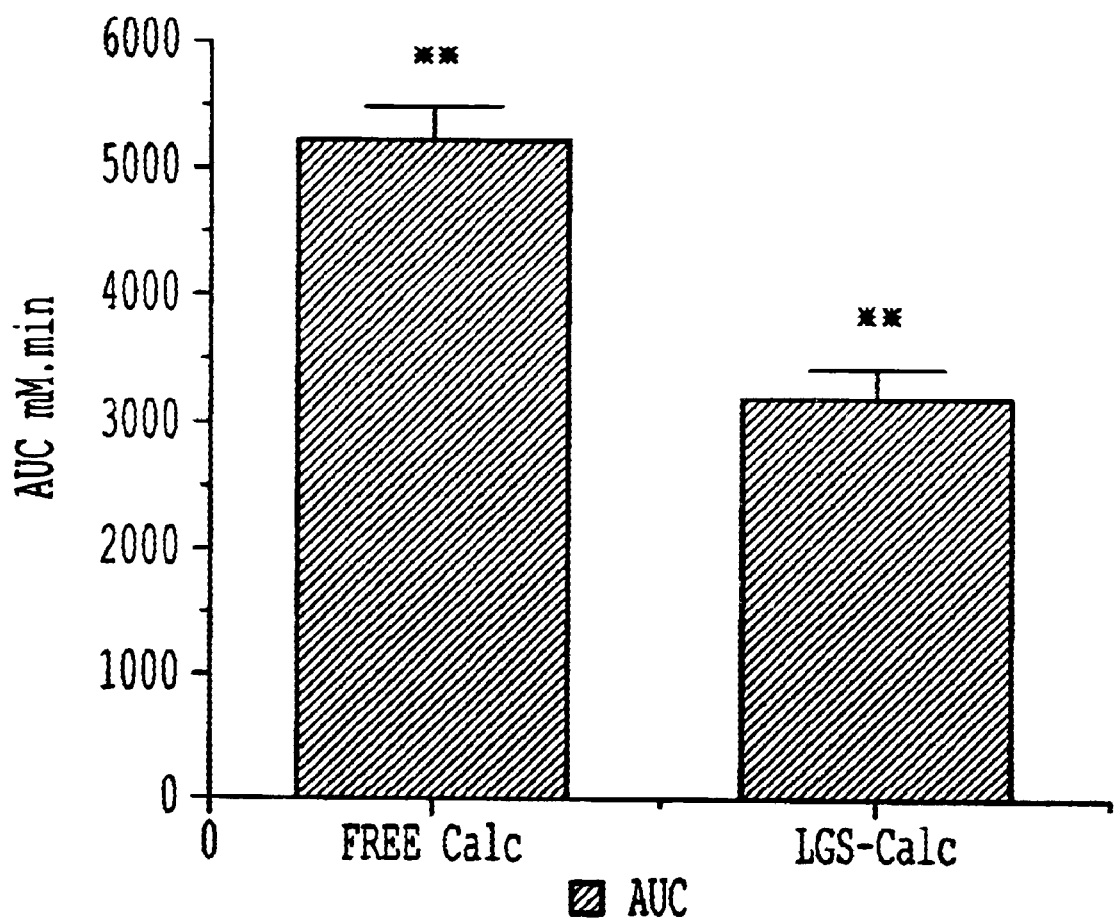

FIG. 6 represents the variations in phosphaturia as a function of time (-■-=LGS-calcitonin vector ((PA-vector) construct) with a molecular weight of at least greater than 500 kDa, which is equal to lipogelosomes® encapsulating calcitonin with a diameter at least greater than 40 nm), -□-=free calcitonin, -□-=LGS-calcitonin vector ((PA-vector) construct) with a molecular weight at least greater than 300 kDa, which is equal to lipogelosomes® encapsulating calcitonin with a diameter of at least greater than 20 nm);

FIG. 7 represents the variations in the SGOT (IU/l) as a function of time (-□-=free calcitonin; -♦-=LGS-calcitonin vector according to the invention;

FIG. 8 represents the variations in the SGPT (IU/l) as a function of time (-□-=free calcitonin; -♦-=LGS-calcitonin vector according to the invention;

FIG. 9 represents the differences in AUC of the SGPT contents between the groups treated with free calcitonin and those treated with an LGS-calcitonin vector according to the invention.

It should be clearly understood, however, that these examples are given purely by way of illustration of the subject-matter of the invention, of which they do not in any way constitute a limitation.

EXAMPLE 1

Texturometry Measurements on the Mixture of Gelatinizing Agents G1 and G2 a) Materials and Methods

The measurements are carried out on a TA-XT2i machine from the company Rhéo. The study relates to the behaviour of gels consisting of a mixture of gelatin and iota and kappa-carrageenans during breaking and relaxation tests.

Concentration of the Samples

Gelatin/iota/kappa-carrageenan mixture (80/17.5/2.5) at a concentration of 7.5% w/v, in a 5 mM $Na_2HPO_4$ and 0.9 or 2% NaCl medium.

Preparation of a Solution of Gelatinizing Agents

Sodium chloride is dissolved in a mixer fitted with a turbomixer and a planetary member and containing purified water (15 minutes at 10 rpm), the mixer is raised to a temperature of 75° C. (stirring at 10 rpm for 45 minutes), the gelatinizing agents (gelatin, iota-carrageenans and kappa-carrageenans) are added into the mixer, at 75° C., and the turbomixer is set on at 1500 rpm; the duration of the dissolution step is about 30 minutes; the dissolution is complete when the solution is clear and contains no particles in suspension.

Preparation of the Samples

For the relaxation test, 45 ml of gel are poured, while hot, into a flat-bottomed Petri dish with an outside diameter of 92±2 mm. For the breaking test, 30 ml of gel are poured, while hot, into a flat-bottomed crystallizing basin with an outside diameter of 50±2 mm. The gel is obtained by cooling to a temperature of less than or equal to 37° C. The gel maturation time, which corresponds to a maximum hydration of the gels, is 2.5 days at the study temperature and at rest.

Operating Conditions

For the relaxation test, a compression force is applied to the gel for a given period. The mobile element used is an aluminium cylinder with a diameter of 25 mm, with a pre-speed of 1.0 mm/s, a speed of 0.5 mm/s and a post-speed of 10.0 mm/s. The displacement of the mobile element is 1.0 mm for 30 seconds.

For the breaking test, the mobile element used is an ebonite cylinder 10 mm in diameter with a pre-speed, a speed and a post-speed of 1.0 mm/s. The displacement of the mobile element is 12 mm.

b) Results of a Study at 5° C., with an NaCl Content of 0.9%

| | Relaxation (%) |
|---|---|
| minimum value: | 81 ± 2.2 |
| maximum value: | 89 ± 0.8 |
| | Breaking force (g) |
| minimum value: | 1109 ± 25 |
| maximum value: | 1503 ± 35 | c) Results as a Function of Temperature and of Different NaCl Contents

The operating conditions are identical to those described in a), apart from as regards the displacement of the mobile element used in the relaxation test (displacement of 20% of the total thickness of the gel).

| | Relaxation (%) |
|---|---|
| at 5° C. | |
| 0.9% NaCl: | 89 ± 0.8 |
| 2% NaCl: | 90 ± 0.2 |
| at 25° C. | |
| 0.9% NaCl: | 32 ± 3.9 |
| 2% NaCl: | 38 ± 4.4 |
| at 37° C. | |
| 0.9% NaCl: | 36 ± 3.7 |
| 2% NaCl: | 40 ± 4.9 |
| | Breaking force (g) |
| at 5° C. | |
| 0.9% NaCl: | 1413 ± 66 |
| 2% NaCl: | 1114 ± 143 |
| at 25° C. | |
| 0.9% NaCl: | 211 ± 2.7 |
| 2% NaCl: | 173 ± 1.5 |
| at 37° C. | |
| 0.9% NaCl: | 25.7 ± 2.4 |
| 2% NaCl: | 44.7 ± 3.9 |

EXAMPLE 2

Process for Preparing a Pulverulent Vector According to the Invention Containing Calcitonin 1) Preparation of a Dispersion of Liposomes with a Gelatinized Internal Phase (Lipogelosomes®)

| Constituents: | |
| --- | --- |
| Soybean lecithins | 11.915 kg (7.943%) |
| Gelatin B150 | 7.149 kg (4.766%) |
| Iota-carrageenans | 1.565 kg (1.043%) |
| Kappa-carrageenans | 0.222 kg (0.148%) |
| Sucrose | 8.936 kg (5.957%) |
| Sodium chloride | 1.073 kg (0.715%) |
| Purified water | 119.15 kg (79.43%) |
| TOTAL CONTENTS | 150.01 kg (100%) | a) Preparation of a dispersion of liposomes a mixture of:

| | |
| --- | --- |
| Gelatin B150 | 7.149 kg |
| Iota-carrageenans | 1.565 kg |
| Kappa-carrageenans | 0.222 kg |
| Sucrose | 8.936 kg |
| NaCl | 1.073 kg |
| Na$^+$-chenodeoxycholate | 1.131 kg |
| Purified water (qs 150 kg) | 118.00 kg | is premixed in a mixer at a speed of 10 rpm, the planetary member of which rotates at a speed of 1500 rpm for 1.5 hours under vacuum.

b) Incorporation of Calcitonin

Lowering of the pH of the mixture is carried out using concentrated acetic acid (6 N), by successive additions, until a stable pH of 4.5 is reached. 4.075 g of salmon calcitonin (Bachem Calif.), the specific activity of which is 7017 IU/mg, are then added.

c) Incorporation of Phospholipids into the Solution Obtained in a)

The soybean lecithins (11.915 kg) are added to the premix, in a mixer at a speed of 10 rpm, in which the planetary member rotates at a speed of 1500 rpm, for 5 hours under vacuum (→ formation of an emulsion).

Final dispersion by increasing the stirring speeds of the planetary member (25 rpm) and of the turbomixer (2500 rpm) for a period sufficient to obtain a polydispersity of less than 40%.

A dispersion of lipogelosomes® in aqueous phase is obtained.

Negative staining microscopic observations, cryofracture, cryotransmission and atomic force microscopy: vesicles or assemblies of vesicles having the characteristic appearance of phospholipid bilayers; negative staining makes it possible to observe the more or less pronounced presence of an external gelatinizing agent according to the manufacturing and/or separation process chosen.

d) Tangential Filtration

One volume of the dispersion of lipogelosomes®, which dispersion is obtained during the above steps, is diluted in 20 volumes of hot 0.9% NaCl, with stirring. The diluent (0.9% NaCl) will be supplemented with 8.25×10$^{-4}$% of chenodeoxycholate, depending on the presence of this surfactant in the preceding dispersion. The phase not encapsulated is eliminated by continuous hot tangential ultrafiltration. The ultrafiltration is carried out on a membrane with a selective porosity of 300 or 500 kDa, depending on the desired particle size, of the lipogelosomes®. The product obtained is a suspension of lipogelosomes® encapsulating at least 17% salmon calcitonin, in which the diameters of the liposomes range from 20 nm to 500 nm, when the suspension is ultrafiltered through 300 kDa, and from 40 nm to 500 nm when the suspension is ultrafiltered through 500 kDa.

2) Drying of the Dispersion Obtained

The resulting dispersion of lipogelosomes® in aqueous phase is transferred into a dryer under vacuum (50®100 mbar) for about 4 hours. A fairly homogeneous powder of very pale straw-yellow colour is obtained, containing grains with a diameter of between 0.1 mm and 1 mm.

Under the electron microscope, retraction of the lipid vesicles on themselves was observed, on account of dehydration. Furthermore, it is noted that whereas, in the liquid state, the LGSs are often aggregated inside a homogeneous gelatinized matrix in an environment of numerous isolated vesicular structures, the drying step converts this gelatinous matrix into filaments of dry gelatinizing agent at the surface of the aggregates, but also at the surface of the isolated vesicular structures.

As a variant, the drying is carried out as follows: the dispersion of lipogelosomes® in aqueous phase is distributed directly onto a rotating drum dryer (drum temperature: 120–150° C., speed of rotation 3–6 rpm). The "shavings" obtained are then ground and calibrated on a suitable grid. A lipogelosome® (also referred to hereinbelow as LGS) powder having the characteristics defined above is thus obtained.

The drying can be optimized by adding a filler excipient, for example maltodextrin or β-cyclodextrins.

EXAMPLE 3

Comparative Effects of Free or Encapsulated Calcitonin in Vectors Obtained According to Example 2, After Oral Administration to Rats The effects of a preparation according to Example 2 on calcaemia, calciuria, phosphataemia and phosphaturia are analysed in comparison with the oral administration of calcitonin in free form. The pharmacokinetics obtained for the two forms of calcitonin administered are also compared.

Other parameters are also analysed: transaminases (SGOT and SGPT) and glycaemia.

It is important to note that the effect of calcitonin in normocalcaemic rats or man is difficult to demonstrate, and that the responses to this hormone are much sharper when pathological individuals (hypercalcaemic individuals) are treated.

Experimental Protocol

Preparation of LGS-calcitonin

See Example 2.

Animals and Pharmacological Treatment

Animals 10 groups of 10 Wistar Ico rats (IOPS AF/Han, IFFA CREDO), i.e. 100 rats in total, 6 weeks old and weighing between 160 and 180 g, were made up.

The weight of the animals was measured at the start of the experiment in order to ensure, as regards this parameter, a homogeneous distribution of the rats in each of the groups.

The 6 experimental groups are prefed for 7 days on a regime based on sterile "AO4" (UAR=Usine d'Alimentation Rationelle (supplier of regimes)).

The rats are fasted and given glucose ad libitum 24 hours before the administration of the experimental doses.

The weight of the animals is monitored before administration of the experimental doses.

Experimental Scheme

The groups A, B, C, D, E, F, G, H, I and J are made up as follows:

group A: 10 control rats from which plasma and urine are taken at time 0.

group B: 10 rats are intubated and 1.8 ml of 500 kDa LGS-Cal suspension (approximate calcitonin concentration: 54 IU/rat, i.e. 330 IU/kg) are administered to each individual. Plasma and urine are taken at time 45 min.

group C: 10 rats are intubated and 1.8 ml of 500 kDa LGS-Cal suspension (approximate calcitonin concentration: 54 IU/rat, i.e. 330 IU/kg) are administered to each individual. Plasma and urine are taken at time 90 min.

group D: 10 rats are intubated and 1.8 ml of 500 kDa LGS-Cal suspension (approximate calcitonin concentration: 54 IU/rat, i.e. 330 IU/kg) are administered to each individual. Plasma and urine are taken at time 180 min.

group E: 10 rats are intubated and 1.8 ml of 500 kDa LGS-Cal suspension (approximate calcitonin concentration: 54 IU/rat, i.e. 330 IU/kg) are administered to each individual. Plasma and urine are taken at time 300 min.

group F: 10 rats are intubated and 1.8 ml of free calcitonin suspension (concentration: 54 IU/rat, i.e. 330 IU/kg) are administered to each individual. Plasma and urine are taken at time 45 min.

group G: 10 rats are intubated and 1.8 ml of free calcitonin suspension (concentration: 54 IU/rat, i.e. 330 IU/kg) are administered to each individual. Plasma and urine are taken at time 90 min.

group H: 10 rats are intubated and 1.8 ml of free calcitonin suspension (concentration: 54 IU/rat, i.e. 330 IU/kg) are administered to each individual. Plasma and urine are taken at time 180 min.

group I: 10 rats are intubated and 1.8 ml of free calcitonin suspension (concentration: 54 IU/rat, i.e. 330 IU/kg) are administered to each individual. Plasma and urine are taken at time 300 min.

group J: 10 rats are intubated and 1.8 ml of 300 kDa LGS-Cal suspension (approximate calcitonin concentration: 36 IU/rat, i.e. 228 IU/kg) are administered to each individual. Plasma and urine are taken at time 90 min.

Anaesthesias: the anaesthesias are performed using Rompun® (2% xylazine; 10 mg/kg)/Imalgene® (10% Ketamine; 60 mg/kg) via intraperitoneal injection according to the chronology indicated in the experimental scheme.

Sampling

Blood samples are taken from the abdominal aorta by catheterization under anaesthesia, at time 0 for group A; time 45 min for groups B and F; time 90 min for groups C, G and J; time 180 min for groups D and H; time 300 min for groups E and I. The bladder is also cannulated and the urine collected according to the same timing as that used for the taking of the blood samples.

The total plasma will be obtained after separation of the blood samples by centrifugation at 3000 rpm for 15 minutes in tubes containing 3.8% EDTA (non-protein anticoagulant).

Analyses

The calcaemia, phosphataemia and transaminases will be assayed by colorimetry on each sample of plasma.

Statistical Processing of the Data

The results of the measurements are expressed as an average ±SEM for the ten rats in each group. The data will be compared by means of statistical tests suitable for this type of experimental protocol (studies of the parameters and pharmacokinetics). The statistical test chosen is the ANOVA test or analysis of variance, the significances of the differences are determined by the Fisher test and by the Scheffe test which is more discriminating.

Two methods for expressing the results were used: graphic representation of the averages of 10 values relative to the parameter considered, as well as comparative analysis of the AUCs (areas under the curve). This method of expression makes it possible to assess the differences in the amplitudes in the responses obtained.

The results obtained are represented according to the pharmacokinetic technique: variation of the degree of the parameter considered as a function of time. In this instance, it is not a search for a dose effect.

Results

Figure 1:
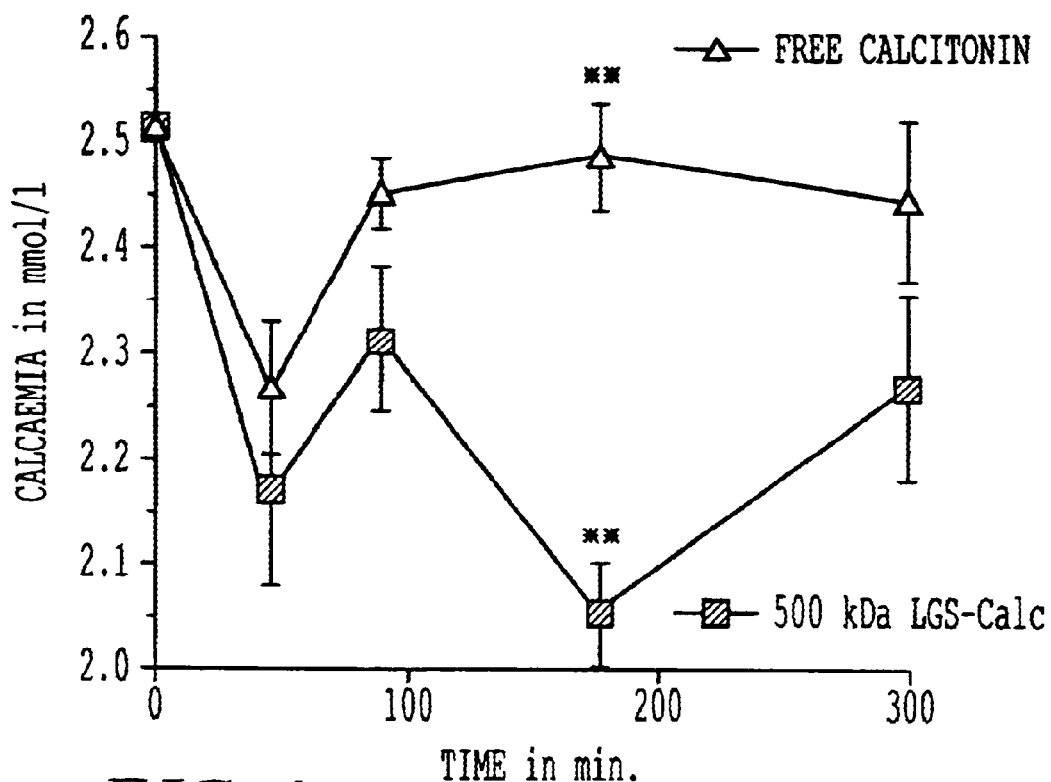

Pharmacokinetics of the Effect of Free Calcitonin or Calcitonin Encapsulated in LGS-Calc Form, on Calcaemia FIG. 1 represents the variations in calcaemia as a function of time. The assays used to determine the calcium concentrations were carried out by the colorimetric method given in the Pharmacopoeia. The basal values of the calcaemias (at time 0) correlate very well with the previous data. Each point represents the average of 10 values, i.e. 9 groups of 10 independent rats. The averages are expressed ±SEM. The results are compared by analysis of variance (ANOVA), for non-paired values. The significant differences are symbolized by **. This symbol corresponds to a significance in the highly discriminating Scheffe test.

A transient decrease in calcaemia after oral administration of free calcitonin is observed. It is explained by the fact that during a massive administration of peptide such as calcitonin, a small percentage crosses the intestinal barrier (1%) without being denatured. In this case, 330 IU were administered, which corresponds to a lymphatic passage of 3.3 IU (passage from the intestinal lumen into the plasma, via the lymphatic canal pathway). However, the IV-route effect of calcitonin starts at 0.9 IU. It is thus normal to observe this effect of free calcitonin. The hypocalcaemia observed after oral administration of calcitonin decreases over time to return to the normal level after 90 min.

As regards the LGS-Calc, the same effect at 45 min is observed, but this hypocalcaemic effect is twice as large at 180 min. This fact indicates that the LGS formulation, for an equivalent calcitonin concentration, is more effective in terms of pharmacological effect than free calcitonin. This two-phase phenomenon can be attributed to the activity of calcitonin associated with the external layer of the LGSs (primary action), and the second effect might be due to the calcitonin contained inside the LGSs. A delay effect doubled by an increase in the activity of the PA by a factor of 2 is thus observed.

Figure 2:
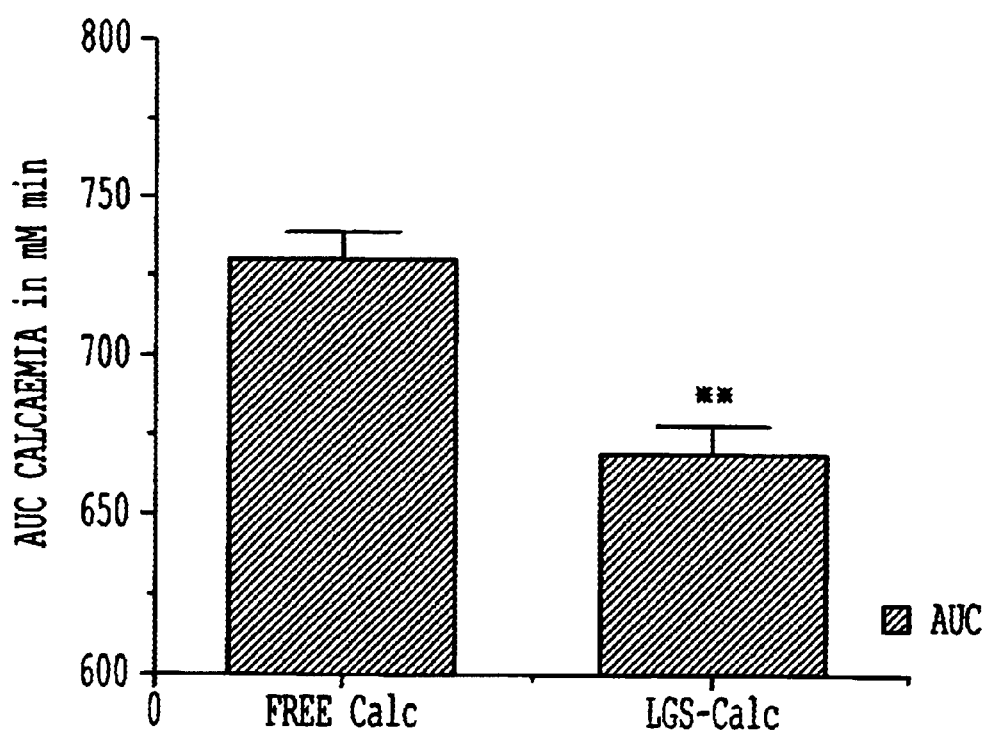

FIG. 2 represents the difference in the AUC between the calcaemia obtained with free calcitonin and that obtained after oral administration of LGS-Calc. The difference observed is highly significant in the Scheffe test. The AUC corresponds to a cumulative of all the values obtained during the experiment; these values are integrated and then compared. The AUC corresponds to the area under the curve for the variations in calcaemia as a function of time. The smaller this AUC, the greater the hypocalcaemiant effect (since the curve then approaches the x-axis).

Figure 3:
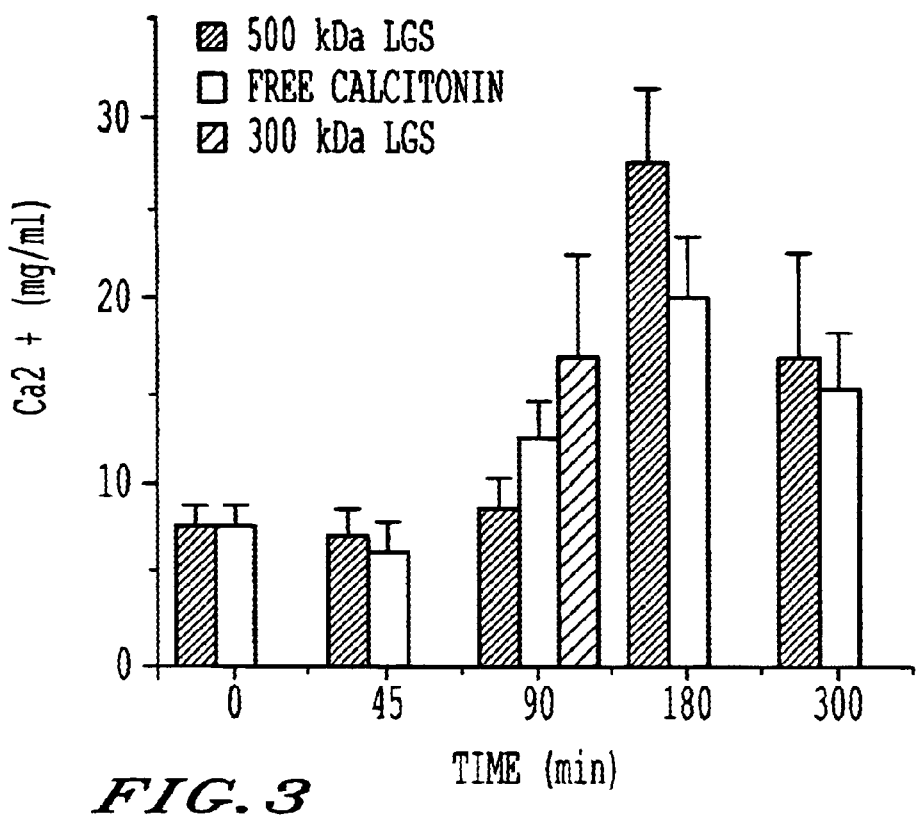
FIG. 3 represents the variations in calciuria as a function of time (-■-=500 kDa LGS-calcitonin vector, -□-=free calcitonin, -□-=300 kDa LGS-calcitonin vector)

Pharmacokinetics of the Effect of Free Calcitonin or Calcitonin Encapsulated in LGS-Calc Form, on Calciuria The restrictions mentioned with regard to the plasmatic results obtained by atomic absorption are confirmed by analysis of the values obtained on the urine of rats treated with free or encapsulated calcitonin. In point of fact, FIG. 3 corroborates the values of FIG. 1, since a hypocalcaemia is always followed by an increase in calciuria.

Figure 4:
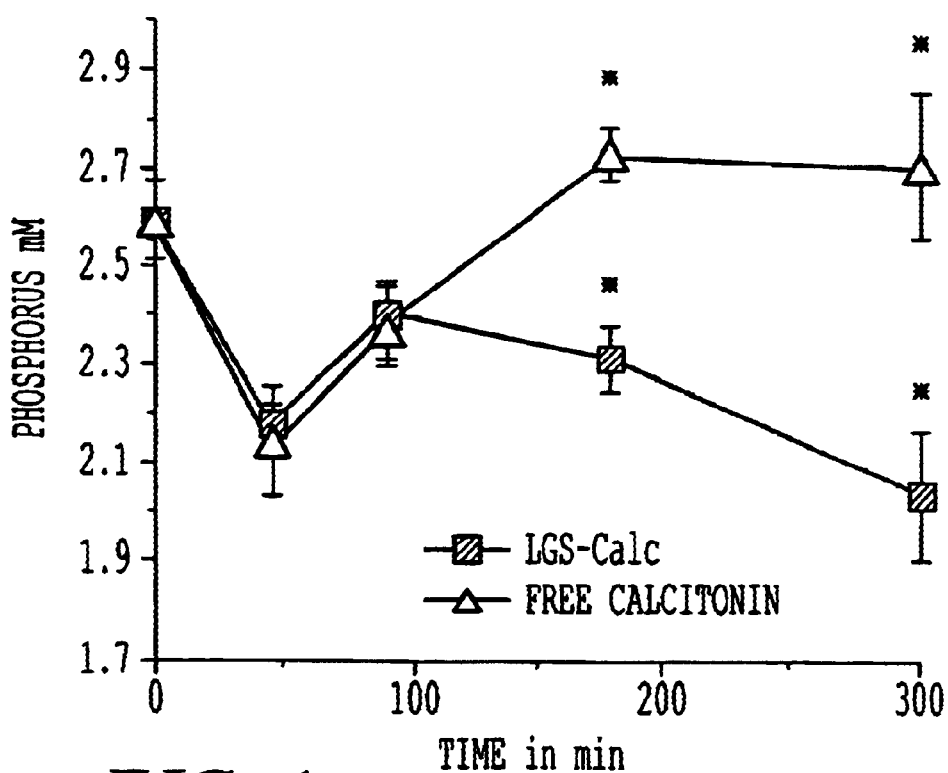
FIG. 4 represents the evaluation of the phosphataemia as a function of time (-D-=free calcitonin; -■-=LGS-calcitonin vector according to the invention)

Pharmacokinetics of the Effect of Free Calcitonin or Calcitonin Encapsulated in LGS-Calc Form, on Phosphataemia (FIG. 4)

Figure 5:
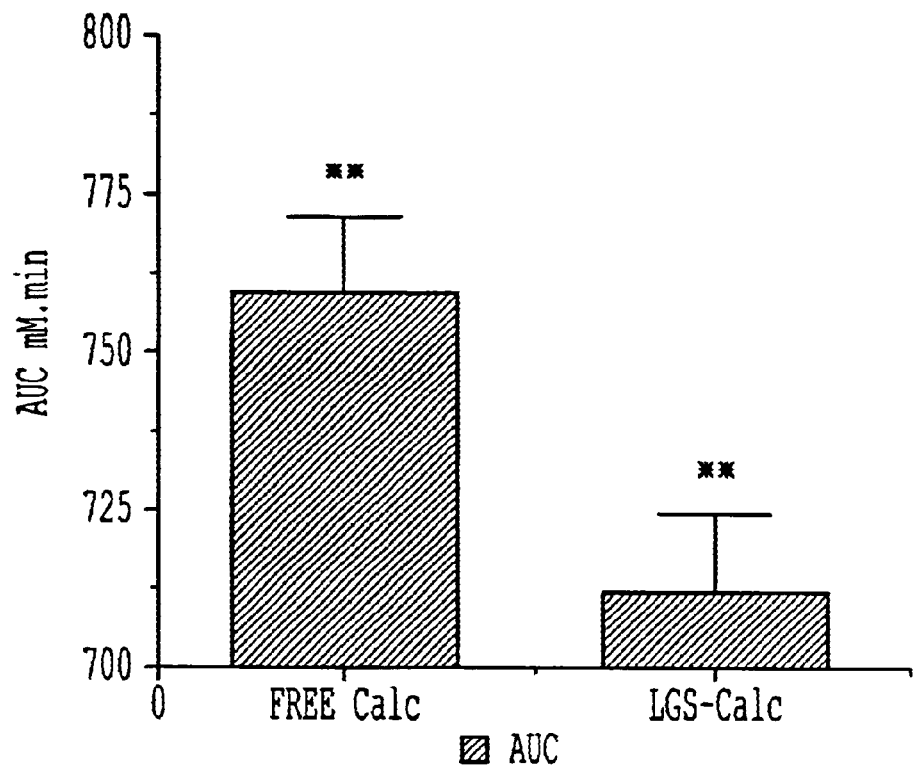
FIG. 5 represents the difference in AUC between the phosphataemia obtained with free calcitonin and that obtained after oral administration of the LGS-calcitonin vector according to the invention.

The LGS-Calc and free calcitonin induce a hypophosphataemia (colorimetric assay) which continues only in the case of the groups treated with LGS-Calc. The results are significant in the Fisher test. The comparison represented in FIG. 5, of the respective AUCs, very clearly confirms the pharmacokinetic data.

The difference between the two AUCs is significant in the Scheffe test.

Pharmacokinetics of the Effect of Free Calcitonin or Calcitonin Encapsulated in the Form of LGS-Calc, on Phosphaturia (FIG. 6)

The assays on the urine samples were carried out by atomic absorption as in the case of the calciuria (see previously).

These results are less significant than in the case of calciuria. It is thus difficult to draw a conclusion. Nevertheless, it appears that at time 180 min, the effect of the LGS-Calc has a tendency to be greater than that of the non-encapsulated drug.

Toxicological Aspect of the Study

By means of the samples taken, it was possible to carry out the assays of the transaminases during the administration of the two active principles. Analysis of the SGOT contents over time shows a tendency towards hypotoxicity (FIG. 7) of the encapsulated form of calcitonin compared with the free form. This difference is very significant in the Fisher test at time 300 min. However, the comparisons of the AUCs do not show any significant differences as regards the variations in the SGOT contents over time.

This tendency towards moderation of the increase in transaminases ("hypotoxicity") is confirmed by analysis of the SGPT contents over time (FIG. 8).

These data show strong hypotoxicity of the encapsulated form of calcitonin compared with the free form. FIG. 9 shows the differences in AUC for the SGPT contents between the groups treated with free calcitonin and those treated with encapsulated calcitonin.

The difference between the two areas is significant in the Scheffe test.

This effect can be used in particular in the context of administration of highly toxic active principles, in order to reduce the hepatotoxic impact of such substances.

Conclusion

The encapsulation of calcitonin in the LGS form potentiates the crossing of the intestinal barrier.

The comparative effect of the oral administration shows a genuine potential of the LGS form, which is all the greater since it is now possible to stabilize this structure in powder form.

The two-phase hypocalcaemiant effect of LGS-Calc can be explained by the distribution of calcitonin at the surface and in the centre of the LGSs.

This experiment makes it possible to evaluate the hypotoxicity of the LGS-Calc form compared with the free form, which appears to be more toxic.

The data demonstrating the superiority of the LGS-Calc form over free calcitonin were acquired using the assay method recommended in the pharmacopoeia.

The two peaks of hypocalcaemia brought about after oral administration of the two forms of PA were specified: 45 and 180 min after administration.

The "delay" effect of the LGS-Calc might be due to a gradual release into the intestine of microspheres obtained from a stock matrix: the LGS-Calc concentrates, which gradually penetrate the intestinal barrier.

EXAMPLE 4

Increase in the Bioavailability of the Principles Encapsulated in the Lipogelosome and Derived Forms; Comparison Between Liposomes and Lipogelosomes®

1. Comparison of Resistance or Stability of the Lipogelosome® (LGS) and Standard Liposome (LS) Forms The LGSs make it possible to prepare pharmaceutical forms (powder) which are impossible to prepare with the conventional liposomal forms; only the LGSs withstand the physiological conditions: pH, temperature, intestinal motility, enzymes, which gives them the capacity to be administered via the oral or pulmonary route, whereas the LSs are destructured when they are administered via such routes.

a) Resistance to pH and to Intestinal Bile Salts

Series of incubations of LGS and of LS, for 1 hour at 37° C. in the presence of bile salt (taurodeoxycholate) with detergent power, and thus destructuring power with respect to lipid vesicles, are carried out. The results show that for a bile salt concentration of 0.25 mM, the LGSs are 3 times as resistant as the LSs. The resistance of the structures is analysed by laser granulometry (variation in the level of counting of the particles, indicated by the variation in the diffraction of a laser, in KHz).

Comparison of the structure (observed by laser granulometry) of LGSs and LSs after incubation for 1 hour at variable pH values shows that the LGSs are stable from pH=2.5 to 9, whereas the LSs are predominantly in tact only at pH=6.3.

The LGSs are more resistant than the LSs to the pH levels and the detergent concentrations encountered in the stomach; this makes it possible to deduce that the LSs are degraded in the stomach, whereas the LGSs are resistant for longer.

b) Resistance to Seric Medium, to Temperature and to Stirring

Series of incubations of LGS and of LS were carried out for 24 hours at 37° C. with stirring. The lipid phases of the LGSs and LSs, which are rigorously identical in terms of composition, were labelled in the same way with an isotope ($^{14}$-C) The products derived from degradation of the two types of structure: LS or LGS, were analysed over time. It appears in the light of the results that the lipid constituents of the LSs are released more easily than the lipid constituents of the LGSs.

These results show that the LGS form is more stable than the LS form.

c) Comparison of the Leakage of the Encapsulated Active Principles from LGSs and from LSs An active principle (AP) of small size (500 Da) was encapsulated in LGSs and in LSs, in the same amount. Thereafter, the two preparations were stirred at 37° C. in a seric medium, and the release of the encapsulated AP was measured. The amount of AP released from the LSs is 60% higher than the amount of AP released from the LGSs (1.6 units of AP for the LS; 1.01 units of AP for the LGS).

By virtue of this significantly higher stability of the LGSs, solid pharmaceutical forms can be prepared and an oral administration is possible, whereas these could not be envisaged with liposomes of conventional formulation.

2. Comparison of the Bioavailability of the Lipogelosome® Form and Conventional Liposome Form, in a Cell Model The differences in cellular internalization of a marker or of an AP when these molecules are encapsulated in LGS (lipogelosome®) forms or in LS (liposome) forms were analysed.

a) Comparison of the Cellular Internalizations of Liposomes and Lipogelosomes®

The LSs and LGSs were labelled using radioactive probes or fluorescent probes and, after a period of incubation in a medium in the presence of human macrophages (THP1 strain) in culture at 37° C., the comparative internalization of the two types of structure (LS and LGS) was analysed at the end of incubation, the incubation times being identical. The analysis of the internalizations was carried out by various analytical methods.

A. Fluorescence Microscopy

The images show an internalization of the LSs and LGSs, but in the case of the LSs, the distribution of the signal is homogeneous, whereas the distribution of the signal for the LGSs is localized in punctiform intracellular structures.

This result shows that the LGSs are degraded less rapidly intracellularly than the LS structures (in which the signal diffuses more rapidly in the cell).

Thus, an effect of slow diffusion of the active principles encapsulated in LGSs appears, whereas it does not exist for the LSs.

B. Radiolabelling

Intracellular counting of the radiolabelled LGSs and radiolabelled LSs shows that the LGSs are internalized 2.5 times as much as the LSs under the same experimental conditions.

The LGSs are internalized in greater amount than the LSs: this fact shows that the cellular bioavailability of LGSs is greater than that of LSs, which is due to the difference between the two liposomal structures: the presence of a specific temperature-reversible gel in the internal phase of the LGS, which radiates out up to the surface of the particle, gives LGSs a preferential cellular uptake property.

C. Flow Cytometry

These experiments are based on the comparative cellular endocytosis of LGS and LS labelled with a fluorescent probe. After incubation, the cells are harvested and then passed to the flow cytometer, which quantifies the fluorescent signal in each cell. The spectra obtained show that the cells incubated with LGSs emit 2.5 times as much fluorescent signal as the cells incubated with LSs.

The LGSs are internalized 2.5 times as much as the LSs: this fact shows that the cellular bioavailability of LGSs is greater than that of LSs.

b) Comparative Cellular Pharmacology of Lipogelosomes®—AP/free AP

A. AZT and 3TC, Effects on Macrophages in Culture

In these experiments, LGSs encapsulating AZT or 3TC were incubated with human macrophage cells. The cytotoxicities of the free products or of the products encapsulated in the LGSs were analysed. The results show that the encapsulated APs are 150 times more effective than free AZT or 3CT, in terms of toxicity with respect to macrophages in culture.

These experiments show that, for equal doses, the encapsulated AP is 150 times more active with respect to macrophages than free AP, which is quite probably due to its better cellular internalization.

B. Doxorubicin and PEG 4000, Effects on Hepatocytes and Differentiated Intestinal Epithelial Cells, in Culture The cellular internalization of two molecules: doxorubicin and PEG 4000, was compared, according to whether they are in free form or encapsulated in the form of LGS.

Under the same experimental conditions of time and concentration, the fact that the molecule is encapsulated brings about an increase in its cellular incorporation or in its pharmacological activity with respect to cells of hepatic or intestinal origin, by a factor ranging from 1.5 to 3.

These experiments show that the bioavailability of the molecules encapsulated in the form of LGS is increased relative to their free form, on intestinal epithelial cells or on hepatic parenchymal cells.

c) Explanation of the Modified Bioavailability of Molecules When They are in the Form of LGSs Liposomes (LS) are usually internalized into cells by a process of membrane fusion, known as passive diffusion, i.e. a process which does not bring into question any second messengers responsible for the expression of a membrane receptor.

However, LGSs differ from LSs by the presence of a specific temperature-reversible gel in the internal phase of the LGS, which radiates out up to the surface of the particle, as well as by the presence of a gel film over its external surface. This gel is of proteo-sugar nature (mixture of gelatin and κ and ι carrageenans).

The differences in cellular internalizations and thus in bioavailability between LSs and the LGSs according to the invention lie essentially in the presence and composition of this gel.

Differentiated or undifferentiated intestinal cells (strains: HT29, HT29gal, T84) were cultured on a semi-porous filter (diffusion chamber). LGSs were incubated with these cells in the presence or absence of cpt-cAMP. In the presence of cpt-cAMP, the internalization of the LGSs is increased by a factor of 2.

This experiment shows that the internalization of LGSs is a cAMP-dependent phenomenon. Moreover, the curve of LGS internalization as a function of the dose shows that the LGS internalization phenomenon is saturable. These two essential facts show that the internalization of LGSs is mediated by a receptor. This internalization process thus differs from processes of endocytosis by fusion of conventional liposomes, which is not dependent on a receptor. Thus, the optimized bioavailability of drugs encapsulated in LGSs is explained by the involvement of a receptor which is specific to LGSs.

d) Bioavailability of the Lipogelosomes® Forms In vivo in Rats see Example 3 e) Bioavailability of the Lipogelosomes® Forms on the Diffusion Chamber Model

Intestinal epithelial cells were cultured to confluence on a semi-porous filter in order to obtain a biocompartmental system, separating a "plasmatic" medium from an "intestinal lumen" medium. LGSs were placed on the "intestinal lumen" side and then, after an incubation period, the "plasmatic" medium was analysed.

In this compartment, laser granulometry reveals structures with the same characteristics as the LGSs deposited at the start of the experiment in the "intestinal lumen" compartment. The addition of a proportion of CDCA (chenodeoxycholate) to the LGS formulation, increases the number of particles found in the "plasmatic" compartment.

These experiments show that a proportion of LGSs crosses the intestinal epithelium, quite probably by a process of paracellular passage or transcytosis. This passage is increased when the LGS formulation is modified by the addition of CDCA.

Thus, it is possible to optimize the intestinal transepithelial passage (after oral administration, for example) of molecules encapsulated in LGSs; the LGS form makes it possible to increase the intestinal bioavailability of the encapsulated molecules, and this property is accentuated when chenodeoxycholate is included in the LGS formulation.

As emerges from the text hereinabove, the invention is not limited in any way to the methods for implementing it, preparing it or applying it which have just been described in greater detail; on the contrary, it encompasses all the variants which may occur to a person skilled in the art, without departing from the context or scope of the present invention.

What is claimed is:

1. A liposomal vector for an active-principle, comprising:
   (a) a pulverulent composition, which comprises unilamellar liposomes, said liposomes, comprising:
      (1) an external lipid phase which consists essentially of phospholipids; and
      (2) an internal aqueous nucleus forming a temperature-reversible aqueous gel which radiates out up to the external lipid phase, which internal aqueous nucleus consists essentially of a mixture M of at least two different non-polymerizable gelatinizing agents G1 and G2, whose gel-sol phase transition point is higher than or equal to 37° C., with G1 being a gelatinizing agent which is selected from the group consisting of gelatin and carrageenans, and G2 being selected from the group consisting of carrageenans whose properties are different from the carrageenans selected for G1, and celluloses;
   which liposomes have a diameter of between 20 nm and 200 nm;
   and wherein the pulverulent composition is present in the form of particulate units which have a mean diameter of between 10 $\mu$m and 1000 $\mu$m and which are formed from one or more of the liposomes which is/are surrounded by a matrix which is selected from the group consisting of a dehydrated temperature-reversible aqueous gel which is selected from the group consisting of gelatin, carrageenans, dextrins and mixtures thereof, such that it contains, on average, from $10^{16}$ to $10^{18}$ liposomes/g of powder; and
   (b) at least one active principle, wherein the active principle is in the gelatinized internal core or in the external lipid phase.

2. The liposomal vector of claim 1, wherein the said internal aqueous nucleus of the liposomes additionally contains at least one glycosidic stabilizing agent or at least one agent for regulating the osmolarity of the medium or at least one surface-active agent or a combination thereof.

3. The liopsomal vector of claim 1, which comprises, in % (m/m):
   from 25 to 75% of phospholipids, from 5 to 45% of gelatinizing agents, from 0 to 70% of glycosidic stabilizing agent, from 0 to 15% of agent for regulating the osmolarity of the medium, from 0 to 20% of surface-active agents and from 0 to 15% of dextrins.

4. The liopsomal vector of claim 1, which comprises from 70 to 95% of gelatinizing agent G1 and from 5 to 30% of gelatinizing agent G2.

5. The liopsomal vector of claim 2, wherein the glycosidic stabilizing agent is sucrose or trehalose.

6. The liopsomal vector of claim 1, wherein the lipids which constitute the external phospholipid phase of the liposomes comprise from 20 to 25% of phosphatidylcholine, from 10 to 18% of phosphatidylethanolamine, and from 9 to 15% of phosphatidylinosilol.

7. The liopsomal vector of claim 1, wherein the lipids which constitute the external phospholipid phase of the said liposomes comprise purified phospholipids, either on their own or in a mixture.

8. A process for preparing the liopsomal vector of claim 1, which the external matrix of the particulate units comprises a dehydrated, temperature-reversible, aqueous gel fraction, said process comprising:
   (1) preparing a dispersion of liposomes having a gelatinized internal nucleus in aqueous phase by:
      (a) preparing a solution of at least one gelatinizing agent, containing a mixture M of gelatinizing agents G1 and G2, by dissolving the said gelatinizing agents while stirring, at a temperature which is higher than the gel-sol phase transition temperature of said gelatinizing agents, in an aqueous solution;
      (b) incorporating the active principle into the solution from (a);
      (c) incorporating lipids into the solution obtained in (b) while stirring the mixture, over a period of less than 5 hours; and
      (d) obtaining a dispersion of liposomes having a gelatinized internal nucleus in an aqueous phase containing the said gelatinizing agents by stirring the emulsion obtained in (c); and
   (2) obtaining the pulverulent product by direct drying of the resulting dispersion.

9. The process of claim 8, wherein step (2) is effected by atomization, coacervation, thin film forming or granulation.

10. A process for preparing the liopsomal vector of claim 1, in which the external matrix of the particulate units comprises a temperature-reversible aqueous gel fraction or a dextrin or both, said process, comprising:
   (1) preparing a dispersion of liposomes having a gelatinized internal nucleus in aqueous phase by:
      (a) preparing a solution of at least one gelatinizing agent, containing a mixture M of gelatinizing agents G1 and G2, by dissolving the said gelatinizing agents while stirring, at a temperature which is higher than the gel-sol phase transition temperature of the said gelatinizing agents, in an aqueous solution;
      (b) incorporating the active principle into the solution from (a);
      (c) incorporating lipids into the solution obtained in (b) while stirring the mixture, over a period of less than 5 hours, and
      (d) obtaining a dispersion of liposomes having a gelatinized internal nucleus in an aqueous liquid phase containing the said gelatinizing agents, by stirring the emulsion obtained in (c);
   (2) at least partially removing the aqueous liquid phase which contains the said gelatinizing agents and in which the said liposomes are dispersed;
   (3) adding at least one suitable dextrin; and
   (4) obtaining the pulverulent composition by drying, by atomization, the product obtained in (3).

11. The process of claim 8, wherein step (2) of at least partially removing the aqueous liquid phase containing the said gelatinizing agents is carried out by dilution or filtration or both.

12. The process of claim 8, wherein the aqueous solution in step (a) comprises an agent for regulating the osmolarity of the medium or a glycosidic stabilizing agent or both.

13. The process of claim 8, wherein step (b) is carried out at a shearing speed of less than 200 s$^{-1}$.

14. A method for the treatment of hypercholesterolaemias in a mammal, which comprises orally administering an effective amount of the liopsomal vector of claim 1, to a mammal in need thereof.

15. A dispersion of a liposomal vector containing liposomes having gelatinized internal nuclei, as defined in claim 1, in an aqueous solution containing the mixture of gelatinizing agents as defined in claim 1, wherein the liposomes exhibit, in said dispersion, the following morphology:

a vesicular structure having a diameter of between 20 nm and 200 nm; and a polydispersity of the liposomes having a gelatinized internal phase of between 10 and 55%.

16. The liposomal vector of claim 1, wherein the active principle is in the gelatinized internal core.

17. The liposomal vector of claim 1, wherein the active principle is in the external lipid phase.

18. The liposomal vector of claim 1, wherein the active protein is a protein.

19. The liposomal vector of claim 1, wherein the active protein is calcitonin, AZT, or 3CT.

* * * * *